(12) United States Patent
AlJanabi et al.

(10) Patent No.: US 10,539,498 B2
(45) Date of Patent: Jan. 21, 2020

(54) HIGH PRESSURE / HIGH TEMPERATURE DYNAMIC MULTIPHASE CORROSION-EROSION SIMULATOR

(71) Applicant: Saudi Arabian Oil Company, Dhahran (SA)

(72) Inventors: Yahya T. AlJanabi, Dhahran (SA); Turki A. Al-Khaldi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 148 days.

(21) Appl. No.: 15/680,769

(22) Filed: Aug. 18, 2017

(65) Prior Publication Data

US 2019/0056305 A1 Feb. 21, 2019

(51) Int. Cl.
*G01N 17/04* (2006.01)
*G01N 3/56* (2006.01)

(52) U.S. Cl.
CPC .......... *G01N 17/046* (2013.01); *G01N 3/567* (2013.01); *G01N 2203/0226* (2013.01)

(58) Field of Classification Search
None
See application file for complete search history.

(56) References Cited

U.S. PATENT DOCUMENTS

| | | |
|---|---|---|
| 2,274,541 A | 2/1942 | Fontana et al. |
| 2,519,323 A | 8/1950 | Shank et al. |
| 2,664,744 A | 1/1954 | Bilhartz et al. |
| 2,897,060 A | 7/1959 | Dieman |
| 3,273,802 A | 9/1966 | Hull, Jr. |
| 3,406,101 A | 10/1968 | Kilpatrick |
| 3,957,440 A | 5/1976 | Aussieker |
| 4,049,525 A | 9/1977 | Dutton et al. |

(Continued)

FOREIGN PATENT DOCUMENTS

CN 2 718 567 Y 8/2005

OTHER PUBLICATIONS

Reddy R. V. et al. "An integrated approach to accurate corrosion prediction," Journal of Petroleum Technology, Society of Petroleum Engineers, US, vol. 58, No. 5, pp. 76-79. May 1, 2006.

(Continued)

*Primary Examiner* — Peter J Macchiarolo
*Assistant Examiner* — Mohammed E Keramet-Amircolai
(74) *Attorney, Agent, or Firm* — Leason Ellis LLP

(57) ABSTRACT

A system for measuring corrosion and corrosion-erosion rates in a high temperature, high pressure multiphase dynamic environment includes a plurality of ring-shaped test coupons disposed within a test vessel in a vertical arrangement relative to one another. A test fluid mixture is added to the vessel and the temperature and pressure are maintained such that the mixture exists in a multiphase condition that has a vertical stratification such that each test coupon is exposed to a different phase and/or combination of phases of the fluid. Impellers can be used to stir the fluid to provide a dynamic environment. The fluid can include particulate matter to simulate real world test conditions. Separator plates can be disposed at different vertical locations within the vessel to maintain separation between various phases of the fluids and further restrict particulate matter from migrating between sections of the test system.

8 Claims, 1 Drawing Sheet

(56) References Cited

U.S. PATENT DOCUMENTS

| | | | |
|---|---|---|---|
| 4,102,770 | A | 7/1978 | Moriarty et al. |
| 4,383,438 | A | 5/1983 | Eaton |
| 4,563,427 | A | 1/1986 | Weiss et al. |
| 4,928,760 | A | 5/1990 | Freitas |
| 5,006,786 | A | 4/1991 | McKubre et al. |
| 5,228,976 | A | 7/1993 | Abys et al. |
| 5,254,310 | A | 10/1993 | Bressan |
| 5,405,513 | A | 4/1995 | Lewis, II et al. |
| 5,413,692 | A | 5/1995 | Abys et al. |
| 5,425,267 | A | 6/1995 | Herrmann et al. |
| 5,503,006 | A | 4/1996 | Babaian-Kibala et al. |
| 6,368,381 | B1 | 4/2002 | King et al. |
| 6,621,263 | B2 | 9/2003 | Al-Janabi et al. |
| 7,127,959 | B2 | 10/2006 | Blum et al. |
| 7,141,150 | B1 | 11/2006 | Welch et al. |
| 7,313,976 | B2 | 1/2008 | Swain et al. |
| 7,320,245 | B2 | 1/2008 | Jaralla |
| 7,392,842 | B2 | 7/2008 | Morgan et al. |
| 8,061,888 | B2 | 11/2011 | Ji et al. |
| 8,105,533 | B2 | 1/2012 | Hisamatsu et al. |
| 8,261,601 | B2 | 9/2012 | Stolle et al. |
| 8,365,601 | B2 | 2/2013 | Minachi et al. |
| 8,408,053 | B2 | 4/2013 | Al-Jutaily |
| 8,513,020 | B2 | 8/2013 | Hehn et al. |
| 8,561,458 | B2 | 10/2013 | Macuch et al. |
| 9,134,222 | B1 | 9/2015 | Graebner |
| 9,145,512 | B2 * | 9/2015 | Al-Mutairi ............... C09K 8/74 |
| 9,476,820 | B2 | 10/2016 | Zhang et al. |
| 2004/0107769 | A1 | 6/2004 | Blum |
| 2008/0257729 | A1 | 10/2008 | Saeed |
| 2010/0155262 | A1 | 6/2010 | Yepez et al. |
| 2011/0283783 | A1 * | 11/2011 | Al-Jutaily ............ G01N 17/046 73/86 |
| 2012/0074969 | A1 | 3/2012 | Snelling et al. |
| 2012/0279599 | A1 * | 11/2012 | Gluskin ................ G01N 17/00 138/97 |
| 2013/0340542 | A1 | 12/2013 | Pires et al. |
| 2014/0123778 | A1 | 5/2014 | Li et al. |
| 2015/0021169 | A1 * | 1/2015 | Smith ...................... B23K 1/20 204/196.01 |
| 2015/0268152 | A1 * | 9/2015 | Friedersdorf .......... G01N 17/04 73/25.01 |
| 2016/0003734 | A1 * | 1/2016 | Mann .................. G01N 17/006 250/339.05 |
| 2016/0169790 | A1 * | 6/2016 | Bennis ................ G01N 17/002 73/114.77 |
| 2016/0363525 | A1 * | 12/2016 | Friedersdorf ............ G01N 3/02 |
| 2017/0030190 | A1 | 2/2017 | Serres et al. |
| 2017/0030508 | A1 * | 2/2017 | Pilloni ................... C12Q 1/689 |

OTHER PUBLICATIONS

Khan, P. et al., "Effect of benzotriazole on corrosion inhibition of copper under flow conditions," Journal of Environmental Chemical Engineering, vol. 3, pp. 10-19. (2015).

Ji, X. et al.," Erosion-Corrosion Behavior of Electrodeposited Amorphous Ni—W—P Coating in Saline-Sand Slurry." Corrosion, vol. 69, No. 6, pp. 593-600. Jun. 2013.

* cited by examiner

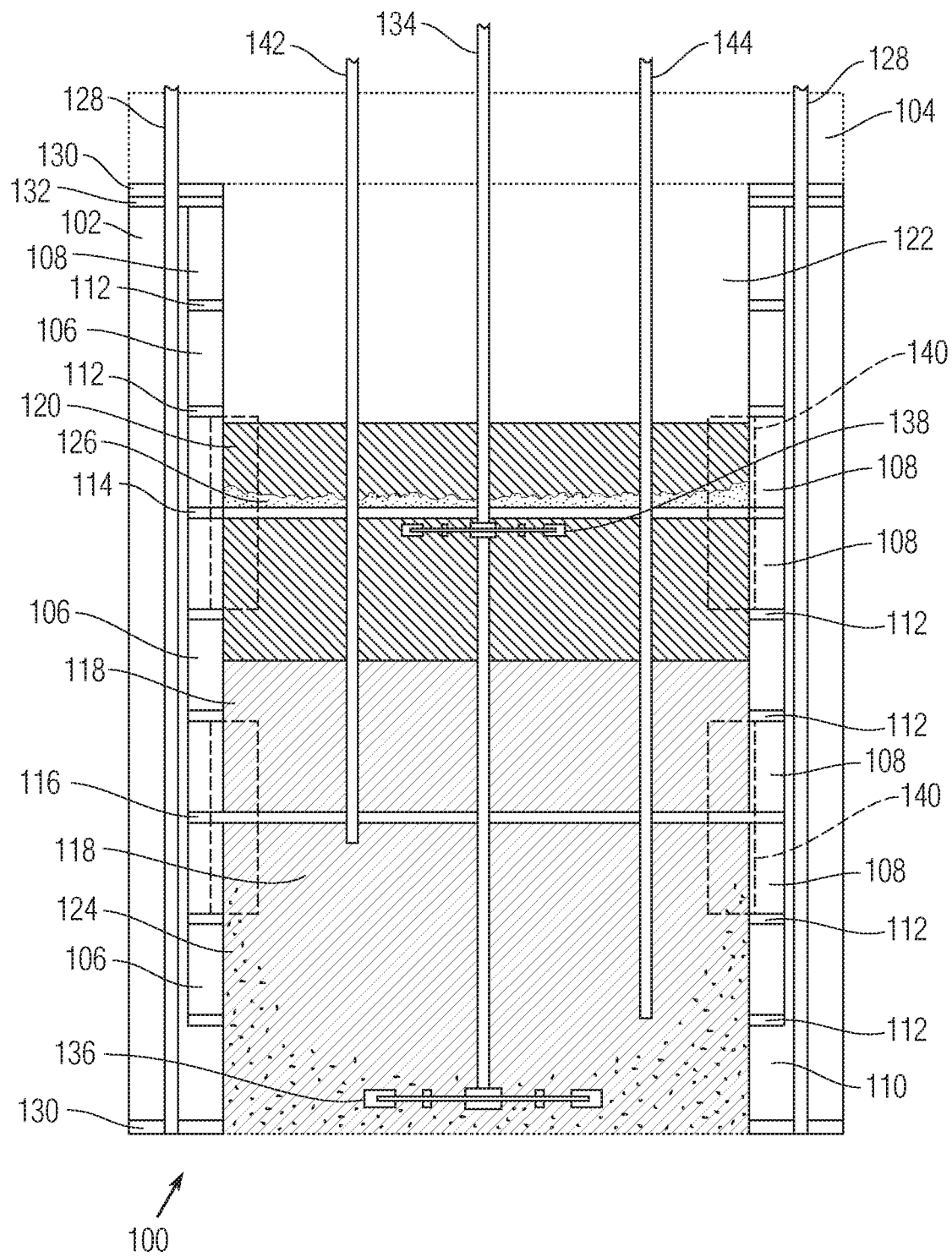

HIGH PRESSURE / HIGH TEMPERATURE DYNAMIC MULTIPHASE CORROSION-EROSION SIMULATOR

FIELD OF THE INVENTION

This patent application generally relates to corrosion testing, and more particularly to systems for high pressure, high temperature multiphase testing.

BACKGROUND OF THE INVENTION

Performing corrosion measurements is often a time consuming process since it typically requires exposing test samples to a corrosive environment for an extended duration of time followed by measurement of the amount of corrosion of the test sample. Typically, one environmental condition is tested during each test process. Accordingly, if varying environments are to be evaluated, several separate corrosion tests must be performed. Moreover, it is often difficult to perform corrosion testing with particulate matter since the particulate matter often contaminates the entire test system. In addition, many severe environment tests are not dynamic in that they lack the ability to stir or agitate the test fluid.

The present invention provides a solution to these and other problems.

SUMMARY OF THE INVENTION

In one aspect of the invention, a high pressure, high temperature dynamic multi-phase testing system for testing corrosive and corrosive-erosive environments by providing a test fluid mixture that is at a different phase at different locations within the system and which is in surrounding relation to a plurality of ring-shaped test coupons is provided. The testing system includes a casing defining an inner section. A plurality of spacer rings are disposed vertically relative to one another and supported by the casing. At least a first, second, and third ring-shaped test coupons among the plurality of ring-shaped test coupons are each disposed between at least two of the plurality of spacer rings. The first, second, and third ring-shaped test coupons are disposed at a respective an upper section, middle section, and lower section of the casing. A plurality of separator plates are provided. One of the plurality of separator plates is disposed between the upper and middle section of the casing and another of the plurality of the separator plates is disposed between the middle and lower section of the casing. The separator plates are configured to maintain a separation between each of the phases of the multi-phase test fluid so that each of the ring-shaped test coupons is exposed to a different phase or combination of phases of the test fluid mixture.

According to a further aspect, a rotor shaft is disposed within the housing and arranged to turn within the test fluid.

According to a still further aspect, which can be combined in an embodiment constructed in accordance with one or more of the foregoing aspects, first and second impellers supported by the rotor shaft and positioned to stir the test fluid within the housing.

According to a yet further aspect, which can be combined in an embodiment constructed in accordance with one or more of the foregoing aspects, one of the first and second impellers is disposed at the lower section of the casing to stir one phase of the test fluid, and wherein the other of the first and second impellers is disposed at the middle section of the casing to stir another phase of the test fluid.

According to a further aspect, which can be combined in an embodiment constructed in accordance with one or more of the foregoing aspects, baffles are supported by the casing and extending into the fluid, wherein the baffles are shaped and arranged to reduce vortex formation in the fluid within the casing.

According to another aspect, which can be combined in an embodiment constructed in accordance with one or more of the foregoing aspects, particulate matter is disposed within the test fluid to simulate additional corrosion and corrosion-erosion conditions.

According to a still further aspect, which can be combined in an embodiment constructed in accordance with one or more of the foregoing aspects, a first particulate matter disposed within one phase of the test fluid and second particulate matter disposed within another phase of the test fluid.

According to a yet further aspect, which can be combined in an embodiment constructed in accordance with one or more of the foregoing aspects, the first particulate matter is sand and the second particulate matter is sulfur.

According to a further aspect, which can be combined in an embodiment constructed in accordance with one or more of the foregoing aspects, the separator plates are positioned to restrict migration of the first and second particulate matter from migrating between respective sections of the casing.

According to another aspect, a method of performing high pressure, high temperature dynamic multi-phase testing system for testing corrosive and corrosive-erosive environments in a test vessel is provided. The method includes the step of preparing a test system. The test system includes a plurality of ring-shaped test coupons and a casing defining an inner section. A plurality of spacer rings are disposed vertically relative to one another and supported by the casing. At least a first, second, and third ring-shaped test coupons among the plurality of ring-shaped test coupons are each disposed between at least two of the plurality of spacer rings. The first, second, and third ring-shaped test coupons are disposed at a respective an upper section, middle section, and lower section of the casing. A plurality of separator plates, wherein one of the plurality of separator plates is disposed between the upper and middle section of the casing and another of the plurality of the separator plates is disposed between the middle and lower section of the casing. The method further includes the step of providing a test fluid mixture that is at a different phase at different locations within the system and which is in surrounding relation to the plurality of ring-shaped test coupons. The separator plates are configured to maintain a separation between each of the phases of the multi-phase test fluid so that each of the ring-shaped test coupons is exposed to a different phase or combination of phases of the test fluid mixture. A temperature and pressure is maintained, for a period of time, within the test vessel, wherein the temperature and pressure simulates a severe environment. The plurality of ring-shaped test coupons are inspected.

BRIEF DESCRIPTION OF THE DRAWING

The accompanying drawing figure illustrates an exemplary embodiment and is not intended to be limiting of the invention.

FIG. 1 illustrates a schematic side view of the testing system according to an embodiment of the invention.

DETAILED DESCRIPTION OF CERTAIN EMBODIMENTS OF THE INVENTION

The invention is now described with reference to the accompanying drawing figure, which forms a part hereof, and which shows, by way of illustration, an example implementation and/or embodiment of the present invention. It is to be understood that other embodiments can be implemented and structural changes can be made without departing from the spirit of the present invention. Among other things, for example, the disclosed subject matter can be embodied as methods, devices, components, or systems.

Furthermore, it is recognized that terms may have nuanced meanings that are suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter can be based upon combinations of individual example embodiments, or combinations of parts of individual example embodiments.

In accordance with the present application, embodiments are provided that are directed to systems and devices for providing screening and evaluation of materials and corrosion inhibitors under dynamic multiphase sour environments at high pressures and high temperatures. As one example, in certain embodiments, the system can operate at severe test conditions of up to 690 bar (10,000 psi) and 260° C. (500° F.). In other examples, the system can operate to test severe conditions over a range conditions between approximately 5,000 psi to 10,000 psi and 250° F. to 500° F. These severe conditions can be tested in a five-liter size autoclave reactor. The testing can be conducted under dynamic conditions, which can be achieved by using radial impellers to stir the test solution. The impellers can be located at a central region of the test vessel and ring-shaped test specimens can be arranged to surround the central region, with the ring-shaped specimens being stationary within the vessel. The test solution can include of various combinations of suspended particles (e.g., sand and/or elemental sulfur), and hydrocarbons (liquids and/or gases) and/or aqueous and gaseous phase fluids (e.g., hydrogen sulfide, carbon dioxide, and oxygen). The corrosion test ring specimens can be installed in a non-metallic insert and can be vertically arranged within the vessel such that respective test ring specimens are exposed to a lower, middle, and upper section of the test vessel. Membranes can be disposed between the respective sections that can restrict the migration of suspended particles between the respective sections of the test vessel (e.g., restrict sand particles and/or sulfur solids from moving from one section to another). The membranes can also minimize vortex formation in the test fluid, especially during dynamic stirring of the test fluid. The test system can further be configured such as placing sand and elemental sulfur within the middle section of the test vessel.

The test system can further include a rotating shaft to which the impellers are attached for stirring rotation. The system can include two impellers, one supported at a lower section of the shaft to stir the lower section of the vessel and another supported at middle section of the shaft to stir the middle section of the vessel. The rotation of the impellers can, for example, create high wall shear stresses in the test fluid at the lower section of the vessel, and simulate flow patterns at a liquid-gas interface of the test fluid at the middle section of the vessel. The vertical positions of the impellers along the shaft within the vessel are adjustable. The use of ring-shaped test specimens (as opposed to rectangular-shaped flat test specimens) helps to ensure that the test specimens retain residual stresses typically found in downhole tubulars and surface flow lines and trunklines and, therefore, more accurate simulation of actual conditions can be provided.

Referring now to FIG. 1, one example of an embodiment of a test system as described above is shown. The test system 100 includes an outer casing 102. The casing 102 can be a non-metallic material such as, for example, a polyamide-imide (e.g., Torlon). The casing can be inserted into an autoclave test vessel (not shown) made from a corrosion resistant material such as Hastelloy C276. The casing 102 can be sized and shaped such that a space 104 (represented by the dashed space above the casing in FIG. 1) is provided between the top of the casing 102 and the autoclave head (e.g., cover, not shown). The casing 102 forms a part of an assembly that supports ring-shaped test specimens 106. Three test specimens 106 can be included with one located at a lower section of the casing, and middle section of the casing, and an upper section of the casing, which corresponds to a lower, middle, and upper section of the test vessel, respectively. Non-metallic rings 108 (e.g., a polyamide-imide material) can be interspersed between the test specimens 106 that can act as spacers between adjacent test specimens. The bottom section of the casing 102 can include a shoulder 110 that provides spacing for the lower test ring 106 and also provides a bearing surface against which the test rings 106 and spacer rings 108 can be seated against, as discussed in more detail below. Non-metallic washers 112 (e.g., polyether ether ketone (PEEK)) can be disposed on an upper and lower side of each test specimen 106.

An upper separator 114 and a lower separator 116 can be disposed within the casing (e.g., sandwiched between adjacent rings 108) to define a boundary between the lower, middle, and upper sections of the test vessel. Accordingly, the lower section of the vessel can contain an aqueous phase 118 of the test fluid, the middle section of the vessel can contain a combination of an aqueous phase 118 and hydrocarbon phase 120 of the test fluid, the upper section of the vessel can contain a combination of a hydrocarbon phase 120 and gaseous phase 122 of the test fluids, as shown in FIG. 1. Other phase distributions within the vessel can be provided. The upper 114 and lower separators 116 can be made from a corrosion resistant material such as PEEK or Hastelloy C276.

In certain arrangements, the test fluid can include combination of particulate matter suspended within various phases of the fluid at various locations in the test vessel. For example, as shown in FIG. 1, the lower section contains sand particles 124 in the aqueous phase 118 of the test fluid and the upper section contains solid elemental sulfur 126 (e.g., pellets or crystals) in the hydrocarbon phase 120 of the fluid. As shown, the upper separator 114 helps restrict movement of the sulfur 126 from migrating from the upper section to the middle section, for example. The lower separator 116 helps restrict movement of the sand particles 124 from migrating from the lower section to the middle section, for example.

To complete the casing assembly, fasteners 128 (e.g., stud bolts made from a corrosion resistant material such as Hastelloy C276) extend from an upper section of the casing 102 through to the bottom of the casing. Washers 130 (e.g., metallic, corrosion resistant Hastelloy C276) are disposed at the upper and lower sections of the fasteners 128. A non-metallic washer 132 (e.g., PEEK) can be provided under the upper washers 130. The combination of test rings 106, spacer rings 108, and separators 114, 116 can be seated against the lower shoulder 110 of the casing 102 and the fasteners 128 and washers 130, 132 help maintain these elements in an assembled form.

A rotor shaft 134 can be centrally disposed within the vessel and can support a first impeller 136 and a second impeller 138. The first impeller 136 can be larger than the second impeller 138, in certain embodiments. The first impeller 136 can be arranged so as to be disposed at a lower section of the rotor shaft 134. The second impeller 138 can be arranged so as to be disposed at a middle section of the rotor shaft. Different arrangements can be constructed while having the impellers suitably positioned relative to the test fluid. Thus, the first impeller 136 can be positioned to stir the lower section of the vessel which contains the aqueous phase 118 of the test fluids and the second impeller 138 can be positioned to stir the middle section of the vessel which contains the hydrocarbon phase 120 of the test fluids. In one embodiment, the first and second impellers can be 6-flat-blade disc turbines and be made from a corrosion resistant material (e.g., Hastelloy C276). Rotation of the rotor shaft 134 cause rotation of the first and second impellers, which provides controlled stirring of the test fluid. Baffles 140 (shown in dashed lines) can extend from the casing and into the test fluid. The baffles 140 help prevent vortex formation in the fluid during stirring, which can cause unreliable test results.

The system can further include a pH electrode 142 to measure the pH levels of the test fluid and an oxygen electrode to measure the amount of dissolved oxygen in the test fluid. A dip/purge tube 144 can also be provided.

Accordingly, the combination of ring-shaped test samples, stirring impellers, multiphase test fluids, separator membranes, and suspended particles provides for an efficient system for corrosion and erosion testing samples in a high pressure, high temperature environment. The ring-shaped test samples better approximate real life structures (e.g., pipes) and so test results will be more accurate. The impellers provide for stirring of the test fluid, which provides for a dynamic environment that more closely approximates real life conditions for more accurate tests. Inclusion of various solid particles in the fluid further enhances the testing. Sand solid particles can be used to simulate erosion and erosion-corrosion processes, while elemental sulfur particles can be used to simulate aggressive corrosion attacks by deposited sulfur on downhole tubing and casings. Moreover, the multiphase environment in combination with the separator plates permits corrosion tests to be performed for a variety of conditions with a single test. The test system 100, which includes the ring-shaped test pieces and spacers, can be placed into a test vessel that is sized and shaped to receive the test system 100 and be capable of operating under severe test conditions of high temperature and high pressure. Test fluid and solid particles can be added into the test vessel. The temperature and pressure can be raised to simulate severe environmental conditions (e.g., as one example, between 5,000-10,000 psi and 250° F.-500° F.). The impellers can be used to stir the fluid mixture to simulate dynamic conditions. After a period of time, the ring-shaped test pieces can be removed and the rate of corrosion and/or corrosion-erosion can be evaluated.

Notably, the accompanying figure(s) and examples above are not meant to limit the scope of the present application to a single implementation, as other implementations are possible by way of interchange of some or all of the described or illustrated elements. Moreover, where certain elements of the present application can be partially or fully implemented using known components, only those portions of such known components that are necessary for an understanding of the present application are described, and detailed descriptions of other portions of such known components are omitted so as not to obscure the application. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present application encompasses present and future known equivalents to the known components referred to herein by way of illustration.

The foregoing description of the specific implementations will so fully reveal the general nature of the application that others can, by applying knowledge within the skill of the relevant art(s) (including the contents of the documents cited and incorporated by reference herein), readily modify and/or adapt for various applications such specific implementations, without undue experimentation, without departing from the general concept of the present application. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the invention.

While various implementations of the present application have been described above, it should be understood that they have been presented by way of example, and not limitation. It would be apparent to one skilled in the relevant art(s) that various changes in form and detail could be made therein without departing from the spirit and scope of the application. Thus, the present application should not be limited by any of the above-described example implementations.

What is claimed:

1. A high pressure, high temperature dynamic multi-phase testing system for testing corrosive and corrosive-erosive environments by providing a test fluid mixture that is at a different phase at different locations within the system and which is in surrounding relation to a plurality of ring-shaped test coupons, comprising:
    a casing defining an inner section;
    a plurality of spacer rings disposed vertically relative to one another and supported by the casing;
    wherein at least a first, second, and third ring-shaped test coupons among the plurality of ring-shaped test coupons are each disposed between at least two of the plurality of spacer rings, wherein the first, second, and third ring-shaped test coupons are disposed at a respective an upper section, middle section, and lower section of the casing;
    a plurality of separator plates, wherein one of the plurality of separator plates is disposed between the upper and middle section of the casing and another of the plurality of separator plates is disposed between the middle and lower section of the casing;
    a rotor shaft disposed within the housing and arranged to turn within the test fluids;

first and second impellers supported by the rotor shaft and positioned to stir the test fluids within the housing, wherein the separator plates are configured to maintain a separation between each of the phases of the multi-phase test fluids so that each of the ring-shaped test coupons is exposed to a different phase or combination of phases of the test fluids.

2. The test system according to claim 1, wherein one of the first and second impellers is disposed at the lower section of the casing to stir one phase of the test fluids, and wherein the other of the first and second impellers is disposed at the middle section of the casing to stir another phase of the test fluids.

3. The test system according to claim 1, further comprising baffles supported by the casing and extending into the fluid, wherein the baffles are shaped and arranged to reduce vortex formation in the fluid within the casing.

4. The test system according to claim 1, further comprising particulate matter disposed within the test fluid to simulate additional corrosion and corrosion-erosion conditions.

5. The test system according to claim 1, further comprising a first particulate matter disposed within one phase of the test fluid and second particulate matter disposed within another phase of the test fluid.

6. The test system according to claim 5, wherein the first particulate matter is sand and the second particulate matter is sulfur.

7. The test system according to claim 5, wherein the separator plates are positioned to restrict migration of the first and second particulate matter from migrating between respective sections of the casing.

8. A method of performing high pressure, high temperature dynamic multi-phase testing system for testing corrosive and corrosive-erosive environments in a test vessel, comprising the steps of:

preparing a test system, the test system including:
   a plurality of ring-shaped test coupons;
   a casing defining an inner section;
   a plurality of spacer rings disposed vertically relative to one another and supported by the casing;
   wherein at least a first, second, and third ring-shaped test coupons among the plurality of ring-shaped test coupons are each disposed between at least two of the plurality of spacer rings, wherein the first, second, and third ring-shaped test coupons are disposed at a respective an upper section, middle section, and lower section of the casing; and
   a plurality of separator plates, wherein one of the plurality of separator plates is disposed between the upper and middle section of the casing and another of the plurality of the separator plates is disposed between the middle and lower section of the casing;
   a rotor shaft disposed within the housing and arranged to turn within the test fluids;
   first and second impellers supported by the rotor shaft and positioned to stir the test fluids within the housing,
providing a test fluid mixture that is at a different phase at different locations within the system and which is in surrounding relation to the plurality of ring-shaped test coupons, wherein the separator plates are configured to maintain a separation between each of the phases of the multi-phase test fluids so that each of the ring-shaped test coupons is exposed to a different phase or combination of phases of the test fluids;
maintaining, for a period of time, a temperature and pressure within the test vessel, wherein the temperature and pressure simulate a severe environment; and
inspecting the plurality of ring-shaped test coupons for corrosive and corrosive-erosive effects.

* * * * *